(12) United States Patent
Revilla et al.

(10) Patent No.: US 12,359,249 B2
(45) Date of Patent: Jul. 15, 2025

(54) DEVICE FOR ANALYZING A FLUID SAMPLE

(71) Applicant: FLUXERGY, INC., Irvine, CA (US)

(72) Inventors: Ryan Alan Revilla, Costa Mesa, CA (US); Roy James Heltsley, Foothill Ranch, CA (US); Steve Hoe Lee, Glendale, CA (US); Farzad Izadi Kharazi, Encinitas, CA (US); Tej Rushikesh Patel, Carlsbad, CA (US)

(73) Assignee: Fluxergy, Inc., Irvine, CA (US)

( * ) Notice: Subject to any disclaimer, the term of this patent is extended or adjusted under 35 U.S.C. 154(b) by 0 days.

(21) Appl. No.: 17/823,708

(22) Filed: Aug. 31, 2022

(65) Prior Publication Data

US 2022/0411851 A1 Dec. 29, 2022

Related U.S. Application Data

(63) Continuation of application No. 17/850,364, filed on Jun. 27, 2022, now abandoned, which is a continuation of application No. 15/185,640, filed on Jun. 17, 2016, now Pat. No. 11,371,091.

(60) Provisional application No. 62/187,471, filed on Jul. 1, 2015, provisional application No. 62/182,992, filed on Jun. 22, 2015.

(51) Int. Cl.
| | | |
|---|---|---|
| *C12Q 1/686* | (2018.01) | |
| *B01L 3/00* | (2006.01) | |
| *G01N 21/64* | (2006.01) | |
| *G01N 35/00* | (2006.01) | |
| *B01L 7/00* | (2006.01) | |

(52) U.S. Cl.
CPC ........ *C12Q 1/686* (2013.01); *B01L 3/502715* (2013.01); *G01N 21/6428* (2013.01); *G01N 35/00029* (2013.01); *B01L 7/52* (2013.01); *B01L 2200/04* (2013.01); *B01L 2300/0645* (2013.01); *B01L 2400/049* (2013.01); *G01N 2035/00148* (2013.01)

(58) Field of Classification Search
CPC .......... B01L 2200/04; B01L 2400/049; B01L 3/502715; B01L 7/52; G01N 2035/00148; G01N 21/6428; G01N 35/00029; C12Q 1/686
See application file for complete search history.

(56) References Cited

U.S. PATENT DOCUMENTS

| | | |
|---|---|---|
| 5,147,606 A | 9/1992 | Charlton et al. |
| 5,229,297 A | 7/1993 | Schnipelsky et al. |
| 5,726,026 A | 3/1998 | Wilding et al. |
| 5,976,336 A | 11/1999 | Dubrow et al. |
| 6,068,752 A | 5/2000 | Dubrow et al. |
| 6,071,478 A | 6/2000 | Chow |
| 6,114,122 A | 9/2000 | Besemer et al. |
| 6,153,073 A | 11/2000 | Dubrow et al. |
| 6,235,175 B1 | 5/2001 | Dubrow et al. |
| 6,303,343 B1 | 10/2001 | Kopf-Sill |
| 6,399,025 B1 | 6/2002 | Chow |
| 6,428,987 B2 | 8/2002 | Franzen |
| 6,437,551 B1 | 8/2002 | Krulevitch et al. |
| 6,509,186 B1 | 1/2003 | Zou et al. |
| 6,576,459 B2 | 6/2003 | Miles et al. |
| 6,976,336 B2 | 12/2005 | Hartz et al. |
| 7,033,474 B1 | 4/2006 | Dubrow et al. |
| 7,309,467 B2 | 12/2007 | Chen et al. |
| 7,431,888 B2 | 10/2008 | Frechet et al. |
| 7,678,336 B2 | 3/2010 | Chang et al. |
| 7,811,523 B2 | 10/2010 | Bjorneson |
| 7,867,754 B1 | 1/2011 | Regnier et al. |
| 7,883,669 B2 | 2/2011 | Sun et al. |
| 7,915,030 B2 | 3/2011 | Inoue et al. |
| 7,919,062 B2 | 4/2011 | Yuen |
| 7,981,237 B2 | 7/2011 | Park et al. |
| 8,053,239 B2 | 11/2011 | Wheeler et al. |
| 8,158,926 B2 | 4/2012 | Feng et al. |
| 8,202,491 B2 | 6/2012 | Masters et al. |

(Continued)

FOREIGN PATENT DOCUMENTS

| | | | |
|---|---|---|---|
| DE | 202018102600 U1 | 7/2018 | |
| EP | 2863332 A1 * | 4/2015 | ......... G06F 21/6245 |

(Continued)

OTHER PUBLICATIONS

Extended European Search Report Appt. No. 16815096.9 dated Mar. 3, 2019—10 pages.
International Preliminary Report on Patentability issued in related International Patent Application No. PCT/US2016/038152 on Jun. 28, 2017.
Miralles et al., "A Review of Heating Temperature Control in Microfluidic Systems: Techniques and Applications," Diagnostics, 2013, No. 3, pp. 33-67.
Hsieh et al., "Enhancement of thermal uniformity for a microthermal cycler and its applicaiton for polymerase chain reaction," Sensors and Actuators, B 130 (2008), pp. 848-856.
International Preliminary Report on Patentability issued in related International Patent Application No. PCT/US2016/038124 on Jun. 26, 2017.

(Continued)

*Primary Examiner* — Young J Kim
(74) *Attorney, Agent, or Firm* — Armstrong Teasdale LLP

(57) ABSTRACT

Apparatuses and methods related to a point-of-care portable assay device are described herein. In an embodiment, a device for analyzing a fluid sample includes a fluid actuation source configured to engage a port on a test card. The fluid actuation source is configured to apply pressure to the port to cause the fluid sample to move along a microchannel of the test card to enable one or more assays to be performed. The device also includes a controller configured to receive an indication as to which one or more assays are to be performed, cause the fluid actuation source to move the fluid sample into one or more regions on the test card, cause a plurality of electrical contacts to provide power to the test card for performing the one or more assays, and determine at least one test result based on the performed assays.

19 Claims, 11 Drawing Sheets

(56) References Cited

U.S. PATENT DOCUMENTS

| | | |
|---|---|---|
| 8,216,827 B2 | 7/2012 | Pouteau et al. |
| 8,247,176 B2 | 8/2012 | Pourahmadi et al. |
| 8,289,519 B2 | 10/2012 | Ziare et al. |
| 8,343,778 B2 | 1/2013 | Li et al. |
| 8,349,276 B2 | 1/2013 | Paluma et al. |
| 8,367,021 B2 | 2/2013 | Kennedy et al. |
| 8,394,341 B2 | 3/2013 | Reinhardt et al. |
| 8,409,848 B2 | 4/2013 | Zeng et al. |
| 8,540,946 B2 | 9/2013 | Padmanabhan et al. |
| 8,557,199 B2 | 10/2013 | Heath et al. |
| 8,557,518 B2 | 10/2013 | Jovanovich et al. |
| 8,562,918 B2 | 10/2013 | Jovanovich et al. |
| 8,592,157 B2 | 11/2013 | Pourahmadi et al. |
| 8,597,574 B2 | 12/2013 | Bumbrecht et al. |
| 8,603,414 B2 | 12/2013 | Omuro et al. |
| 8,606,414 B2 | 12/2013 | Ludwig |
| 8,790,595 B2 | 7/2014 | Polwart et al. |
| 8,852,527 B2 | 10/2014 | Thomas et al. |
| 8,874,273 B2 | 10/2014 | Sun et al. |
| 8,894,946 B2 | 11/2014 | Nielsen et al. |
| 8,911,636 B2 | 12/2014 | Gautham |
| 8,911,989 B2 | 12/2014 | Lee et al. |
| 8,936,762 B2 | 1/2015 | Ehrlich et al. |
| 8,940,147 B1 | 1/2015 | Bartsch et al. |
| 8,962,252 B2 | 2/2015 | Liang et al. |
| 9,017,946 B2 | 4/2015 | Hasson |
| 9,114,398 B2 | 8/2015 | Knight et al. |
| 9,138,744 B2 | 9/2015 | Tsao et al. |
| 9,170,138 B2 | 10/2015 | Giovangrandi et al. |
| 9,328,344 B2 | 5/2016 | Link et al. |
| 9,335,247 B2 | 5/2016 | Sharpe et al. |
| 9,364,833 B2 | 6/2016 | Bergstedt |
| 9,540,686 B2 | 1/2017 | Zeng et al. |
| 10,761,019 B2 | 9/2020 | Khodadad et al. |
| 11,371,091 B2 * | 6/2022 | Revilla ............... G01N 21/6428 |
| 11,692,967 B2 | 7/2023 | Koussa et al. |
| 2001/0029793 A1 | 10/2001 | Moler et al. |
| 2001/0045355 A1 | 11/2001 | Gephart et al. |
| 2003/0082568 A1 | 5/2003 | Phan et al. |
| 2003/0155344 A1 | 8/2003 | Cobb |
| 2003/0190608 A1 | 10/2003 | Blackburn |
| 2004/0037739 A1 | 2/2004 | McNeely et al. |
| 2004/0193202 A1 | 9/2004 | Allen |
| 2005/0032204 A1 | 2/2005 | Rodgers et al. |
| 2005/0196779 A1 | 9/2005 | Ho et al. |
| 2005/0233440 A1 | 10/2005 | Scurati et al. |
| 2006/0013725 A1 | 1/2006 | Larsen |
| 2006/0094028 A1 | 5/2006 | Danna et al. |
| 2007/0015179 A1 | 1/2007 | Klapperich |
| 2007/0154895 A1 | 7/2007 | Spaid et al. |
| 2007/0163175 A1 | 7/2007 | Kihara et al. |
| 2007/0190828 A1 | 8/2007 | Goldman et al. |
| 2007/0259348 A1 | 11/2007 | Phadke et al. |
| 2008/0200343 A1 | 8/2008 | Clemens et al. |
| 2008/0241910 A1 | 10/2008 | Jung et al. |
| 2008/0253633 A1 | 10/2008 | Xia et al. |
| 2009/0004732 A1 | 1/2009 | LaBarre et al. |
| 2009/0053726 A1 | 2/2009 | Owen et al. |
| 2009/0062134 A1 | 3/2009 | Linton et al. |
| 2009/0140170 A1 | 6/2009 | Nevill et al. |
| 2009/0143233 A1 | 6/2009 | Knight et al. |
| 2009/0186404 A1 | 7/2009 | Kim et al. |
| 2009/0215157 A1 | 8/2009 | Jung et al. |
| 2009/0215194 A1 | 8/2009 | Magni et al. |
| 2009/0311717 A1 | 12/2009 | De Sonneville et al. |
| 2010/0203521 A1 | 8/2010 | Klapperich et al. |
| 2010/0261286 A1 | 10/2010 | Kim et al. |
| 2010/0291584 A1 | 11/2010 | Tseng et al. |
| 2010/0304986 A1 | 12/2010 | Chen et al. |
| 2011/0020876 A1 | 1/2011 | Wilding et al. |
| 2011/0039280 A1 | 2/2011 | Leary et al. |
| 2011/0117673 A1 | 5/2011 | Johnson et al. |
| 2011/0162439 A1 | 7/2011 | Ayliffe |
| 2011/0206545 A1 | 8/2011 | Junod et al. |
| 2011/0269131 A1 | 11/2011 | Chiu et al. |
| 2011/0301535 A1 | 12/2011 | Takayama et al. |
| 2011/0315559 A1 | 12/2011 | Holt et al. |
| 2012/0052560 A1 * | 3/2012 | Knight ............... B01L 3/502746 |
| | | 435/286.1 |
| 2012/0140055 A1 | 6/2012 | Narusawa et al. |
| 2012/0145253 A1 | 6/2012 | Zeng et al. |
| 2012/0195810 A1 | 8/2012 | Cohen et al. |
| 2012/0220047 A1 | 8/2012 | Seifried et al. |
| 2012/0244043 A1 | 9/2012 | LeBlanc et al. |
| 2012/0244604 A1 | 9/2012 | Komilovich |
| 2012/0283108 A1 | 11/2012 | Sampas |
| 2012/0309010 A1 | 12/2012 | Shuber |
| 2013/0052725 A1 | 2/2013 | Yazdanfar |
| 2013/0149215 A1 | 6/2013 | Dekker et al. |
| 2013/0224781 A1 | 8/2013 | Jung et al. |
| 2013/0236907 A1 | 9/2013 | Petersen et al. |
| 2013/0244906 A1 | 9/2013 | Collins |
| 2013/0345096 A1 | 12/2013 | Wan |
| 2014/0038191 A1 | 2/2014 | Liang et al. |
| 2014/0141424 A1 | 5/2014 | Pourahmadi et al. |
| 2014/0161686 A1 | 6/2014 | Bort et al. |
| 2014/0162893 A1 | 6/2014 | Cash et al. |
| 2014/0170672 A1 | 6/2014 | Vandersleen et al. |
| 2014/0199764 A1 | 7/2014 | Domansky et al. |
| 2014/0200154 A1 | 7/2014 | Sugarman et al. |
| 2014/0248621 A1 | 9/2014 | Collins |
| 2014/0295441 A1 | 10/2014 | Egan et al. |
| 2014/0307931 A1 | 10/2014 | Gierahn et al. |
| 2014/0309508 A1 | 10/2014 | Kim et al. |
| 2015/0024426 A1 | 1/2015 | De Oliveira Garcia Da Fonseca et al. |
| 2015/0125947 A1 | 5/2015 | Korczyk et al. |
| 2015/0238967 A1 | 8/2015 | Erickson et al. |
| 2015/0290644 A1 | 10/2015 | Prentice et al. |
| 2016/0033311 A1 | 2/2016 | Giovangrandi et al. |
| 2016/0069913 A1 | 3/2016 | Bakhru et al. |
| 2016/0144356 A1 | 5/2016 | Jung et al. |
| 2016/0144358 A1 | 5/2016 | Patel |
| 2016/0193603 A1 | 7/2016 | Battrell et al. |
| 2016/0296933 A1 | 10/2016 | Chiou et al. |
| 2016/0310948 A1 | 10/2016 | Nowakowski et al. |
| 2016/0318019 A1 | 11/2016 | Ledden et al. |
| 2016/0334351 A1 | 11/2016 | Lu et al. |
| 2016/0340716 A1 | 11/2016 | Ortac et al. |
| 2016/0369323 A1 | 12/2016 | Revilla et al. |
| 2017/0001196 A1 | 1/2017 | Zhang et al. |
| 2017/0008009 A1 | 1/2017 | Azpiroz et al. |
| 2017/0021354 A1 | 1/2017 | Kim et al. |
| 2017/0058324 A1 | 3/2017 | Balog et al. |
| 2018/0015475 A1 | 1/2018 | Arlett et al. |
| 2018/0174689 A1 | 6/2018 | Pulitzer et al. |
| 2019/0160460 A1 | 5/2019 | Keatch et al. |
| 2020/0064254 A1 | 2/2020 | Vanderklein et al. |
| 2020/0383664 A1 | 12/2020 | Loudermilk et al. |
| 2021/0299651 A1 | 9/2021 | McCord et al. |
| 2021/0311042 A1 | 10/2021 | Pamula et al. |
| 2021/0389313 A1 | 12/2021 | Ward et al. |
| 2022/0088583 A1 | 3/2022 | Kleinemolen et al. |
| 2022/0411851 A1 | 12/2022 | Revilla et al. |
| 2023/0116264 A1 | 4/2023 | Basmajian et al. |
| 2023/0175964 A1 | 6/2023 | Taylor et al. |
| 2023/0194540 A1 | 6/2023 | Basmajian et al. |
| 2023/0228674 A1 | 7/2023 | Marrinucci et al. |

FOREIGN PATENT DOCUMENTS

| | | | |
|---|---|---|---|
| WO | 9322053 | 11/1993 | |
| WO | 1993022054 | 11/1993 | |
| WO | WO-0154813 A2 * | 8/2001 | .......... B01F 11/0071 |
| WO | 01/73420 A1 | 10/2001 | |
| WO | 2013177953 A1 | 12/2013 | |
| WO | 2014055963 | 4/2014 | |
| WO | 2014144548 | 9/2014 | |
| WO | 2016209775 A1 | 12/2016 | |
| WO | 2017087834 A1 | 5/2017 | |
| WO | 2021226581 A1 | 11/2021 | |
| WO | 2022029731 A1 | 2/2022 | |

(56) References Cited

FOREIGN PATENT DOCUMENTS

| WO | 2022051703 A1 | 3/2022 |
|----|---------------|--------|
| WO | 2022256514 A1 | 12/2022 |
| WO | 2023059894 A1 | 4/2023 |

OTHER PUBLICATIONS

International Search Report and Written Opinion issued in related International Patent Application No. PCT/US2016/038152 on Sep. 14, 2016. 12 pages.

International Search Report and Written Opinion issued in related International Patent Application No. PCT/US2016/038124 on Sep. 8, 2016. 12 pages.

International Search Report and Written Opinion issued in related International Patent Application No. PCT/US2016/038157 on Oct. 28, 2016. 12 pages.

International Preliminary Report on Patentability issued in related International Patent Application No. PCT/US2016/038157 on Jun. 19, 2017.

Partial European Search Report for EP 23 16 2636, dated Apr. 16, 2024, 12 pages.

Boehm et al., "On-chip microfluidic biosensor for bacterial detection and identification," Sensors and Actuators B, 2007, vol. 126, pp. 508-514.

Cady et al., "Real-time PCR detection of Listeria monocytogenes using an integrated microfluidics platform," Sensors and Actuators B, 2005, vol. 107, pp. 332-341.

Creative Materials Product Description—Dielectric Inks and Coatings Offerings (2015), 2 pages.

Partial Search Report for EP 23161706.9, dated Aug. 4, 2023, 13 pages.

Gubala et al., "Point of Care Diagnostics: Status and Future," Analytical Chemistry, 2012, vol. 84, No. 2, pp. 487-515.

International Search Report and Written Opinion for PCT/US2021/065815, mailed Mar. 24, 2022, 12 pages.

Jarvius et al., "Digital quantification using amplified single-molecule detection," Nature Methods, 2006, vol. 3, No. 9, pp. 725-727, and Supplementary Material.

Liu et al., "Micro air bubble formation and its control during polymerase chain reaction (PCR) in polydimethylsiloxane (PDMS) microreactors," Journal of Micromechanics and Microengineering, 2007, vol. 17, pp. 2055-2064.

Lui et al., "Nucleic Acid-based Detection of Bacterial Pathogens Using Integrated Microfluidic Platform Systems," Sensors, 2009, vol. 9, pp. 3713-3744.

Wang et al., "A miniaturized quantitative polymerase chain reaction system for DNA amplification and detection," Sensors and Actuators B: Chemical, 2009, vol. 141, pp. 329-337.

Wolfe et al., "Evidence of Uncultivated Bacteria in the Adult Female Bladder," Journal of Clinical Microbiology, 2012, vol. 50, No. 4, pp. 1376-1383, and Supplemental Information.

\* cited by examiner

DEVICE FOR ANALYZING A FLUID SAMPLE

PRIORITY CLAIM

This application is a continuation application of U.S. patent application Ser. No. 17/850,364, entitled "Device for Analyzing a Fluid Sample, filed Jun. 27, 2022, which is a continuation application of U.S. patent application Ser. No. 15/185,640, now U.S. Pat. No. 11,371,091, entitled "Device for Analyzing a Fluid Sample and Use of Test Card with Same", filed Jun. 17, 2016, which claims priority to U.S. Provisional Patent Application No. 62/182,992, entitled "Point-Of-Care PCR Assay for Infectious Agents", filed Jun. 22, 2015, and U.S. Provisional Patent Application No. 62/187,471, entitled "Point-Of-Care PCR Assay for Infectious Agents", filed Jul. 1, 2015, the entire contents of each of which are hereby incorporated by reference and relied upon.

FIELD OF THE DISCLOSURE

The present disclosure relates generally to a portable device for a fluid sample assay, and more specifically to a portable device that accepts disposable test cards to quickly and conveniently analyze a plurality of polymerase chain reactions.

BACKGROUND

Point-of-care (POC) in vitro diagnostics tests (IVDT) have traditionally had two major categories, nucleic acid amplification tests (NAAT) or immunoassay-based tests. The former directly detects the pathogen's DNA or RNA, while the latter detects antibodies or antigens generated by the immune system response to the pathogen.

Current POC diagnostic immunoassays lack the high sensitivity and specificity of nucleic acid amplification methods. This becomes more pronounced during the initial stages of infection, often within 168 hours. Taking the case of Dengue virus in whole blood, immunoglobulin M (IgM) and immunoglobulin G (IgG) remain undetectable in the majority of patients until 5 and 10 days post-infection, respectively, whereas nucleic acid can be found as early as 0 to 7 days. Moreover, many immunoassay tests are unable to detect infectious agents until 3 months after the initial onset of the infection. This delay is due to the time it takes for the body's immune system to respond to an infection.

POC diagnostic assays developed utilizing NAATs have very high sensitivities and specificities, matching those of currently accepted laboratory tests. The primary mechanism of NAAT based systems is to directly detect an infectious agent's nucleic acid, lending to the test's ability to detect diseases within the first few days of the onset of infection. In addition, by careful primer design, NAATs also have the ability to have very high specificity and sensitivity compared to immunoassay based testing. The largest drawback of NAATs compared to immunoassay-based tests is the complicated equipment and/or processes required to prepare a sample for testing.

SUMMARY OF THE DISCLOSURE

Described herein are methods and apparatuses related to a point-of-care portable assay device and the use thereof with a test card. In a general embodiment, a device for monitoring a polymerase chain reaction in a fluid sample includes a vacuum source configured to pull the fluid sample through a microchannel, a current source configured to cause the polymerase chain reaction while the fluid sample is located within the microchannel, a light source configured to illuminate the polymerase chain reaction while the current source causes the polymerase chain reaction, a camera imaging device configured to record an image of the polymerase chain reaction while the light source illuminates the polymerase chain reaction, and a controller configured to analyze the image of the polymerase chain reaction and output a resulting analysis of the polymerase chain reaction.

In an example embodiment, the device includes a user interface, wherein the controller is configured to output the resulting analysis to the user interface to be displayed to a user of the device.

In an example embodiment, the image includes at least one of: (i) a plurality of still images of the polymerase chain reaction recorded by the camera imaging device over a period of time; or (ii) a video image of the polymerase chain reaction recorded by the camera imaging device over the period of time.

In an example embodiment, the light source is a fluorescence excitation light source.

In an example embodiment, the current source is configured to cause the polymerase chain reaction by applying a current to electrodes located at a target zone of the microchannel, and wherein the camera imaging device is configured to record the image of the target zone.

In an example embodiment, the device is configured to take a capacitance measurement upstream or downstream of the target zone of the microchannel to determine the presence or absence of fluid within the microchannel.

In a general embodiment, a device for performing an assay on a fluid sample includes a slot configured to receive a test card, a vacuum source configured to align with an outlet port of the test card when the test card is received within the slot, an electrical contact device configured to contact at least one electrical contact of the test card when the test card is received within the slot, a camera imaging device configured to align with a microchannel of the test card when the test card is received within the slot, and a controller configured to (i) cause the vacuum source to pull the fluid sample through the microchannel of the test card when the test card is received within the slot; (ii) cause the electrical contact device to apply current to the at least one electrical contact of the test card while the fluid sample is located within the microchannel; and (iii) cause the camera imaging device to record an image of the microchannel while the fluid sample is located within the microchannel.

In an example embodiment, the controller is configured to cause the electrical contact device to apply current to the at least one electrical contact of the test card to heat the fluid sample while the fluid sample is located within the microchannel.

In an example embodiment, the device includes a light source configured to illuminate at least a portion of the microchannel when the test card is received within the slot.

In an example embodiment, the image includes at least one of: (i) a plurality of still images recorded by the camera imaging device over a period of time; or (ii) a video image recorded by the camera imaging device over the period of time.

In an example embodiment, the outlet port is located on an upper surface of the test card, and the vacuum source is configured to align with the outlet port on the upper surface of the test card.

In an example embodiment, the device includes a button configured to align the vacuum source with the outlet port on the upper surface of the test card.

In an example embodiment, the test card includes an analysis port located on an upper surface of the test card, and the camera imaging system is configured to align with the analysis port on the upper surface of the test card.

In an example embodiment, the at least one electrical contact is located on a bottom surface of the test card, and the electrical contact device is configured to align with the at least one electrical contact on the bottom surface of the test card.

In a general embodiment, a method of analysing a polymerase chain reaction in a fluid sample includes injecting the fluid sample into an inlet port of a test card, placing the test card into an assay device, pulling the fluid sample through a microchannel of the test card, heating the fluid sample to cause the polymerase chain reaction, illuminating the fluid sample during the polymerase chain reaction, and imaging the polymerase chain reaction while the fluid sample is illuminated.

In an example embodiment, imaging the polymerase chain reaction includes recording a plurality of still images of the polymerase chain reaction over a period of time.

In an example embodiment, imaging the polymerase chain reaction includes recording a video of the polymerase chain reaction over a period of time.

In an example embodiment, placing the test card into the imaging device includes aligning a vacuum source with an outlet port of the test card, and pulling the fluid sample through the microchannel of the test card includes pulling a vacuum on the outlet port of the test card.

In an example embodiment, placing the test card into the imaging device includes aligning an electrical contact device with at least one electrical contact of the test card, and heating the fluid sample to cause the polymerase chain reaction includes applying a current to the at least one electrical contact.

In an example embodiment, placing the test card into the imaging device includes aligning a camera imaging device with a target zone of the test card, and imaging the polymerase chain reaction while the fluid sample is illuminated includes recording an image with the camera imaging device.

BRIEF DESCRIPTION OF THE DRAWINGS

Embodiments of the present disclosure will now be explained in further detail by way of example only with reference to the accompanying figures, in which.

DETAILED DESCRIPTION

Before describing in detail the illustrative system and method of the present disclosure, it should be understood and appreciated herein that the present disclosure relates to a rapid, high sensitivity and high specificity, low complexity, diagnostic system 1 using nucleic acid amplification capable of operating in low resource settings. The system described herein is configured, for example, to cause and analyze a polymerase chain reaction (PCR), particularly in the early stages of infection, using a low-cost microfluidic platform employing a PCR with a modified DNA polymerase.

Figure 1:
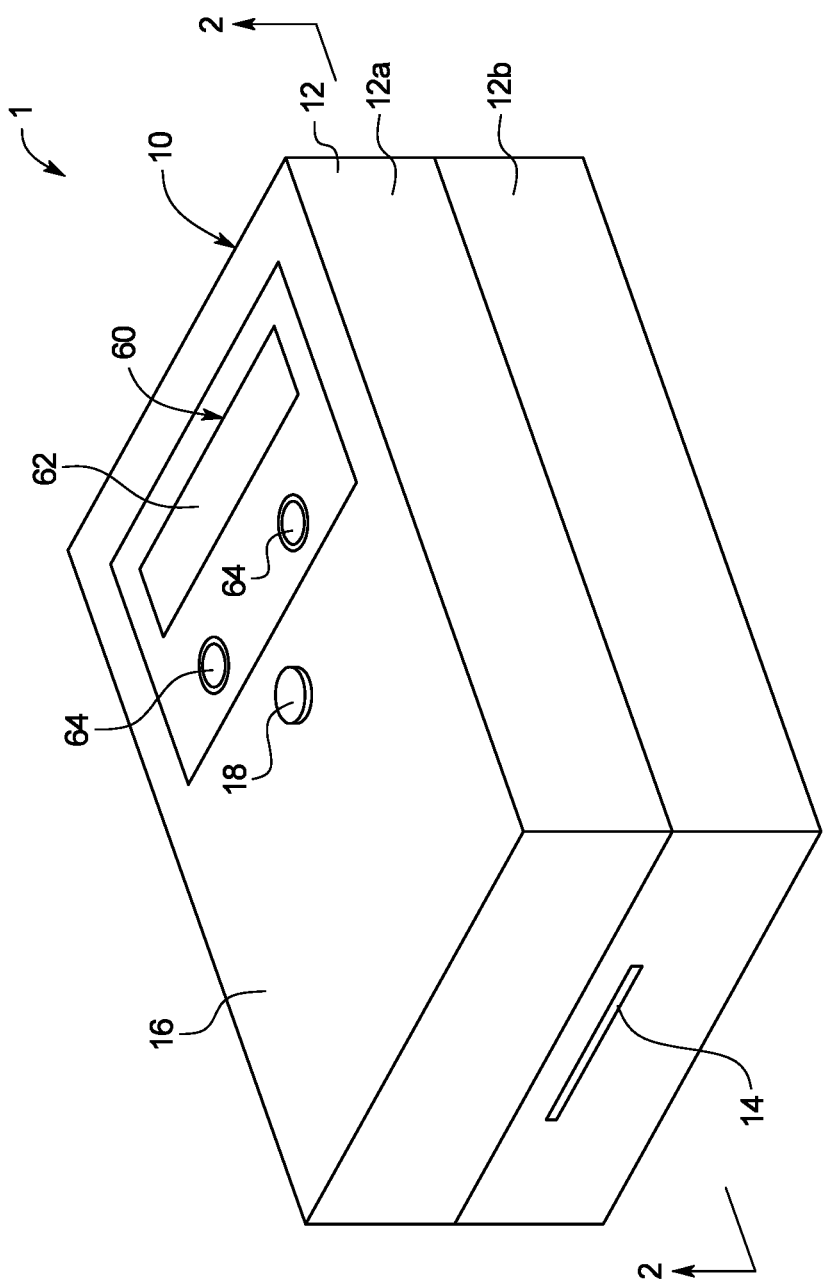
FIG. 1 is a top perspective view of an example embodiment of an assay device according to the present disclosure.

FIG. 1 illustrates an example embodiment of a point-of-care diagnostic system 1 according to the present disclosure. As illustrated, diagnostic system 1 includes an assay device 10 with a housing 12 having a slot 14 to receive a test card 100 (FIGS. 3 to 5), which is an inexpensive disposable test card that can be used with device 10 and then discarded. In use, and as explained in more detail below, a fluid sample can be injected into test card 100, and then test card 100 can be inserted into slot 14 so that device 10 can power test card 100 and analyze a fluid sample within test card 100 without further action by the user. An advantage of diagnostic system 1 is that a plurality of test cards 100 can be used with a single assay device 10 to inexpensively perform a plurality of assays on a single fluid sample or on a plurality of fluid samples. In an embodiment, the assay includes at least one of a polymerase chain reaction (PCR) assay, a flow cytometry assay, or an enzyme-linked immunosorbent assay (ELISA). In an embodiment, the test card 100 is configured to receive about 10 μL of whole blood, the equivalent of a drop of blood obtained from a finger stick. In another embodiment, the fluid sample can be serum, urine, saliva, tears and/or the like.

Housing 12 of assay device 10 is an outer casing for a plurality of electrical components configured to move and analyze the fluid sample within test card 100 when test card 100 is inserted into slot 14. In the illustrated embodiment, housing 12 is formed of a top portion 12a and a bottom portion 12b that can be mated to enclose the plurality of electrical components. Housing 10 can be formed, for example, from a variety of billet or extruded metals and plastics, as well as injection molded plastics. In an embodiment, housing 10 is formed of 6061-T6 Aluminum. As illustrated in more detail below, slot 14 allows test card 100 to be inserted horizontally into housing 12, so that one or more microchannels 134 within test card 100 are aligned horizontally when one or more assays occur within device 10.

Figure 2:
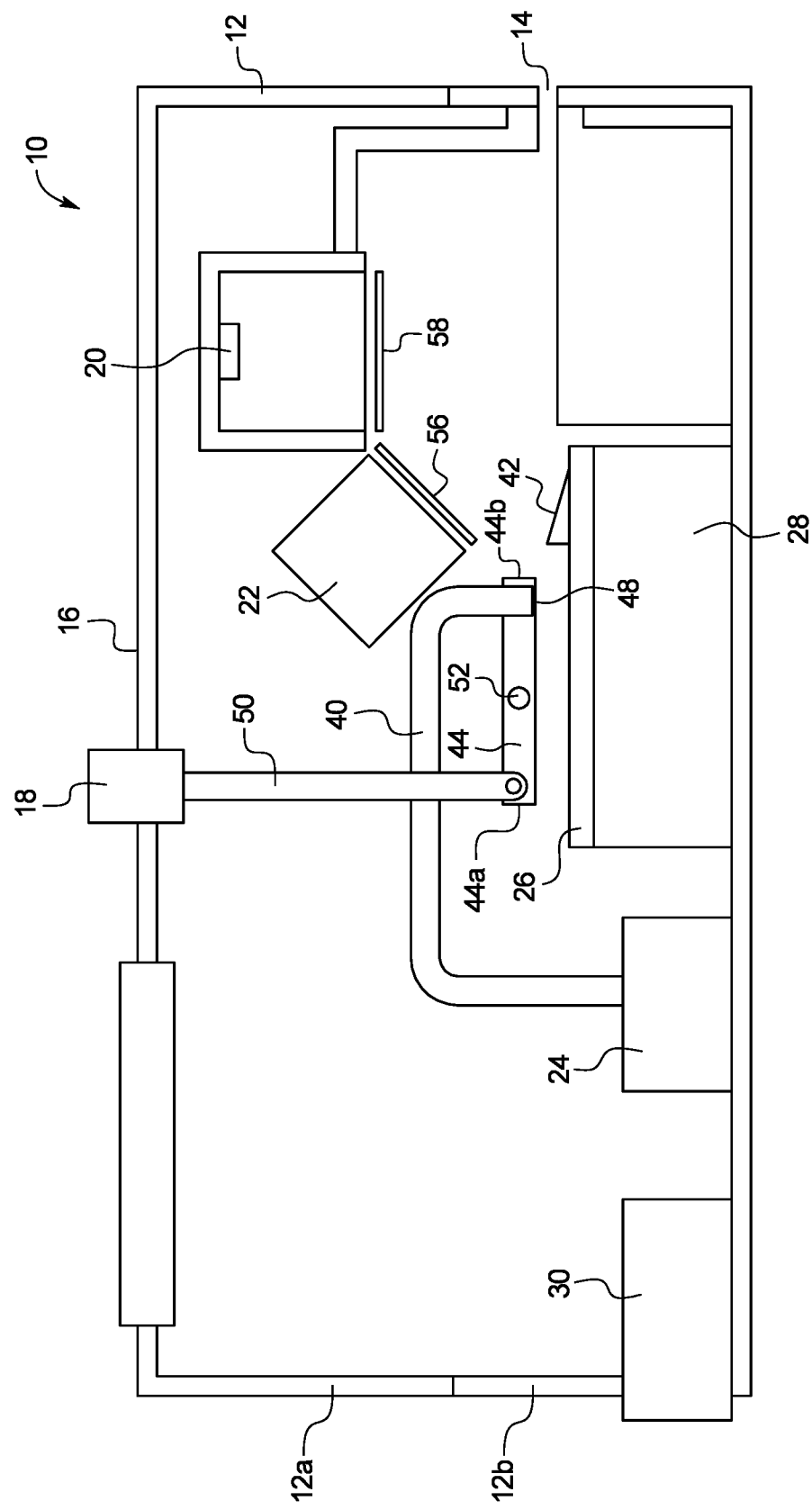
FIG. 2 is a cross-sectional view of the assay device of FIG. 1.

FIG. 2 illustrates a cross sectional view of assay device 10 showing the configuration of the elements located within housing 12, before test card 100 has been inserted into slot 14. Structural elements such as screws and brackets holding the various elements in place in FIG. 2 have been omitted for simplicity. Electrical wiring has also been omitted for simplicity. It should further be understood by those of ordinary skill in the art that the elements located within housing 12 can be arranged in various configurations and still function as described below.

As illustrated in FIG. 2, assay device 10 includes a camera imaging device 20, a light source 22, a fluid actuation source 24, an electrical contact device 26, a controller 28 and a power source 30. In use, and as explained in more detail below, camera imaging device 20, light source 22, fluid actuation source 24, and electrical contact device 26 align with elements of test card 100 as test card 100 is inserted horizontally into slot 14. Once test card 100 is fully inserted into slot 14, controller 28 controls each of camera imaging device 20, light source 22, fluid actuation source 24, electrical contact device 26 and power source 30 to pull a fluid sample through test card 100, heat the fluid sample if necessary for the assay, and analyze the fluid sample.

Figure 3:
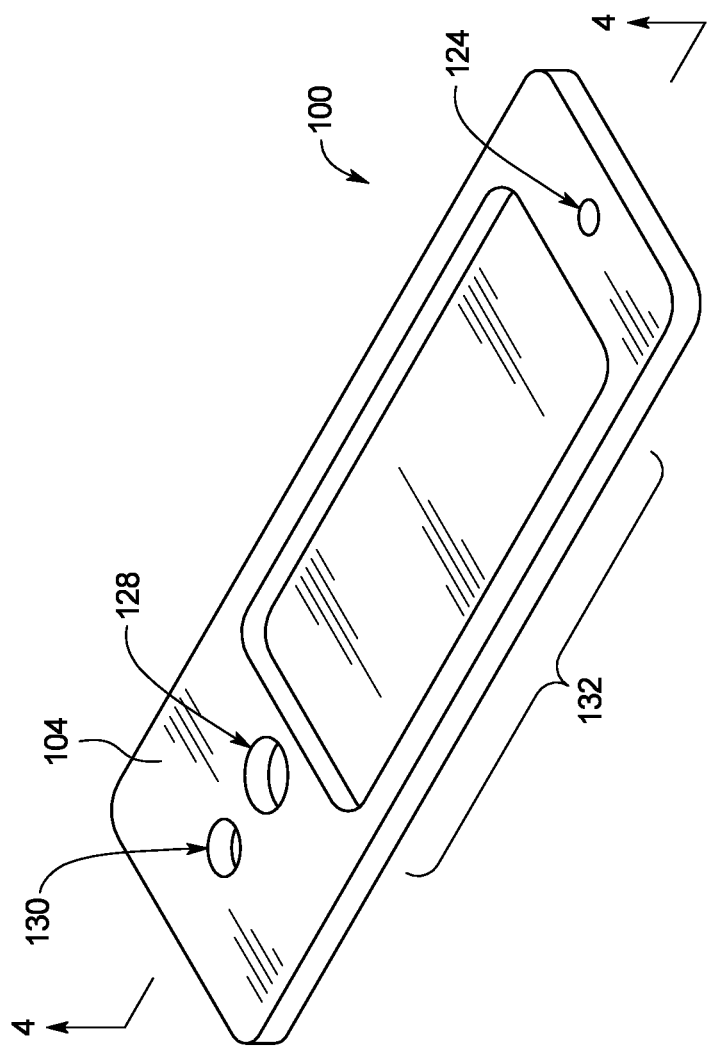
FIG. 3 is a top perspective view of an example embodiment of a test card for use with the assay device of FIG. 1 in a diagnostic system according to the present disclosure.
Figure 4:
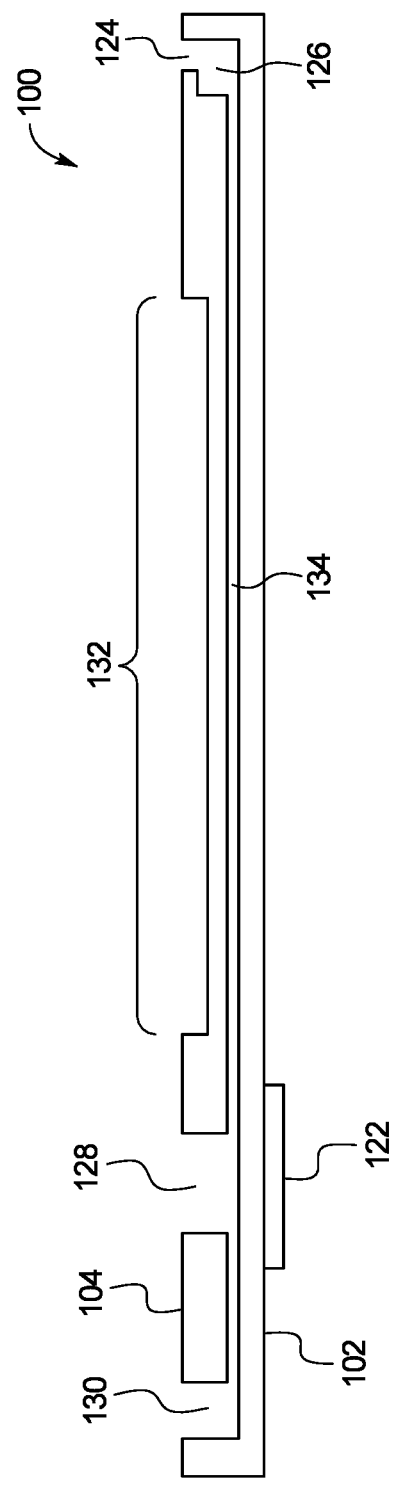
FIG. 4 is a cross-sectional view of the test card of FIG. 3.
Figure 5:
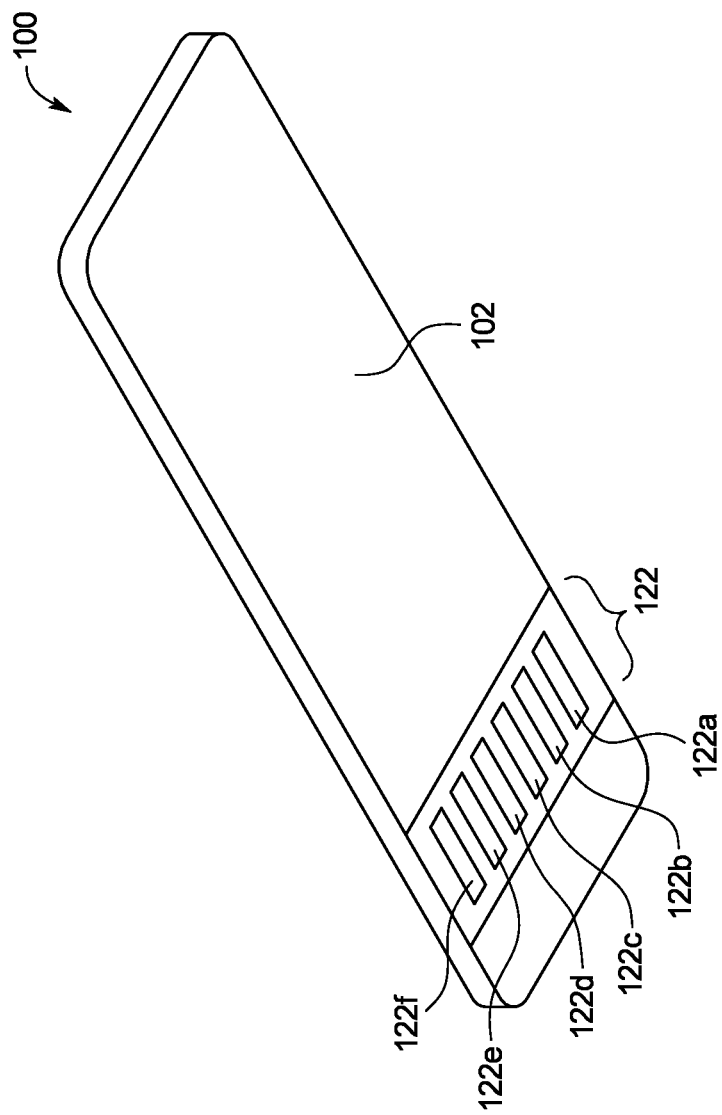
FIG. 5 is a bottom perspective view of the test card of FIG. 3.

FIGS. 3 to 5 illustrate an example embodiment of a test card 100 configured to be inserted into slot 14. Example embodiments of test card 100 are described in more detail in U.S. application Ser. No. 15/185,661, entitled "Test Card for Assay and Method of Manufacturing Same", the entire disclosure of which, and specifically the test card structure disclosure, is incorporated herein by reference and relied upon. Those of ordinary skill in the art will recognize other configurations of test cards 100 that can be used with device 10.

As illustrated, test card 100 includes an inlet port 124, a mixing chamber 126, a capture port 128, an outlet port 130, and a fluid microchannel 134. In use, a liquid sample can be injected into inlet port 124 and mix with a reagent in mixing chamber 126, and then test card 100 can be placed into slot 14 of assay device 10. As explained in more detail below, once test card 100 has been placed within assay device 10, the fluid sample can be pulled though fluid microchannel 134, so that the fluid sample can be analyzed through an analysis port 132 on an upper surface 104 of test card 100. Test card 100 also includes electrical contacts 122 on a bottom surface 102 thereof, which enable electrodes adjacent to fluid microchannel 134 to be controlled to heat fluid within fluid microchannel 134, track fluid flow through fluid microchannel 134, and/or measure properties of fluid within microchannel 134 such as the quantity of the chemical species in the fluid sample.

As explained in more detail in U.S. application Ser. No. 15/185,661, fluid microchannel 134 of test card 100 includes a target zone 166 and optionally a first fluid detection zone 150 upstream of target zone 166 and/or a second fluid detection zone 154 downstream of target zone 166. Target zone 166, first fluid detection zone 150 and second fluid detection zone 154 include respective electrodes 160, 162, 164, which, for example, are screen printed on test card 100 using a dielectric ink. When a current is applied to electrodes 162 of target zone 166, the current across electrodes 162 can heat the fluid sample within target zone 166 to cause a PCR. Electrodes 160 and 164 of first fluid detection zone 150 and second fluid detection zone 154, respectively, form capacitance sensors that can be used to detect whether or not the fluid sample is present within first fluid detection zone 50 and/or second fluid detection zone 154, as the dielectric constant of the capacitance sensors differs considerably when there is liquid in the microchannel. In another embodiment of an ion selective electrode test card, the electrodes can be used, for example, to measure the potential difference between two reactive electrodes within test card 100's microchannels 134 allowing for the measurement of various blood analytes such as sodium levels.

In an alternative embodiment, any of electrodes 160, 162, 164 can be used for a specific chemical species detection. When a fluid sample is present within microchannel 134, the dielectric constant across the electrodes will change depending on the quantity of the chemical species in the fluid sample. If microchannel 134 is located adjacent to a capacitor, then the amount of chemical species can be measured based on the measured capacitance across the electrodes. For example, during a PCR, there is initially very little DNA present, so there will be a very small dielectric constant. As the PCR progresses, the dielectric value will change as more DNA is produced. Any of electrodes 160, 162, 164 can therefore be used to measure a specific chemical species by detecting the dielectric value of the fluid sample.

As illustrated in FIG. 5, the bottom surface 102 of test card 100 includes a plurality of electrical contacts 122, individually labeled as electrical contacts 122a, 122b, 122c, 122d, 122e and 122f. The electrical contacts 122 are in electrical contact with electrodes 160, 162, 164, so that a current applied to electrical contacts 122 can transmitted to electrodes 164 to cause a PCR and/or transmitted to electrodes 160 and 162 to monitor fluid within fluid microchannel 134. Electrical contacts 122 can also be multiplexed, allowing for both the application and measurement of AC and DC voltage and current.

Figure 6A:
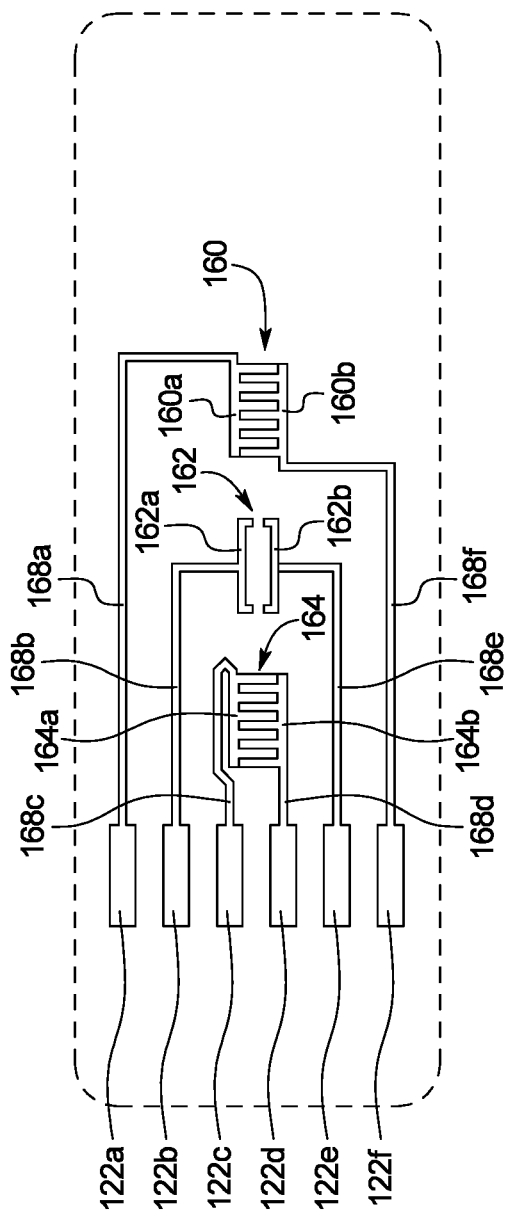
FIG. 6A is a top view of the schematics of the electrical contacts of the test card of FIG. 3.
Figure 6B:
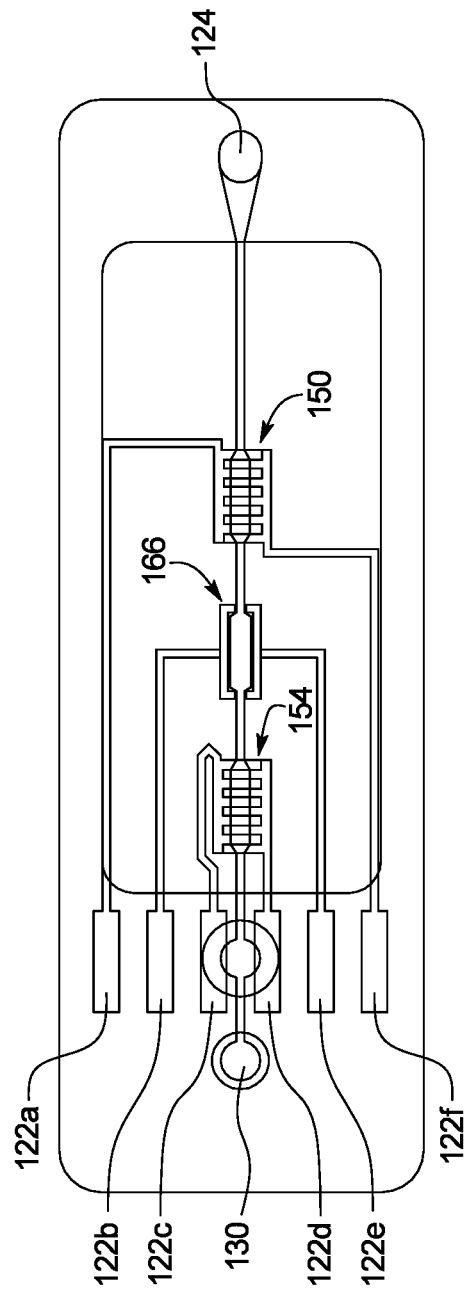
FIG. 6B is a top view of the schematics of the electrical contacts of the test card of FIG. 3 aligned with the microchannel of the test card.

FIGS. 6A and 6B illustrate an example embodiment of the specific electrical connections of electrical contacts 122a, 122b, 122c, 122d, 122e and 122f. FIG. 6A shows the electrical connections without fluid microchannel 134, and FIG. 6B shows the electrical connections aligned with fluid microchannel.

In the illustrated embodiment, electrical contact 122a is electrically connected via electrical line 168a to a first plurality of electrodes 160a of electrodes 160 of first fluid detection zone 150, and electrical contact 122f is electrically connected via electrical line 168f to a second plurality of electrodes 160b of electrodes 160 of first fluid detection zone 150. Electrical contact 122b is electrically connected via electrical line 168b to a first electrode 162a of electrodes 162 of target zone 166, and electrical contact 122e is electrically connected via electrical line 168e to a second electrode 162b of electrodes 162 of target zone 166. Electrical contact 122c is electrically connected via electrical line 168c to a first plurality of electrodes 164a of electrodes 164 of second fluid detection zone 154, and electrical contact 122d is electrically connected via electrical line 168d to a second plurality of electrodes 164b of electrodes 164 of second fluid detection zone 154. Operation of target zone 166, first fluid detection zone 150 and second fluid detection zone 154 by applying a current to one or more of electrical contacts 122a, 122b, 122c, 122d, 122e and 122f is discussed in more detail below.

Figure 7:
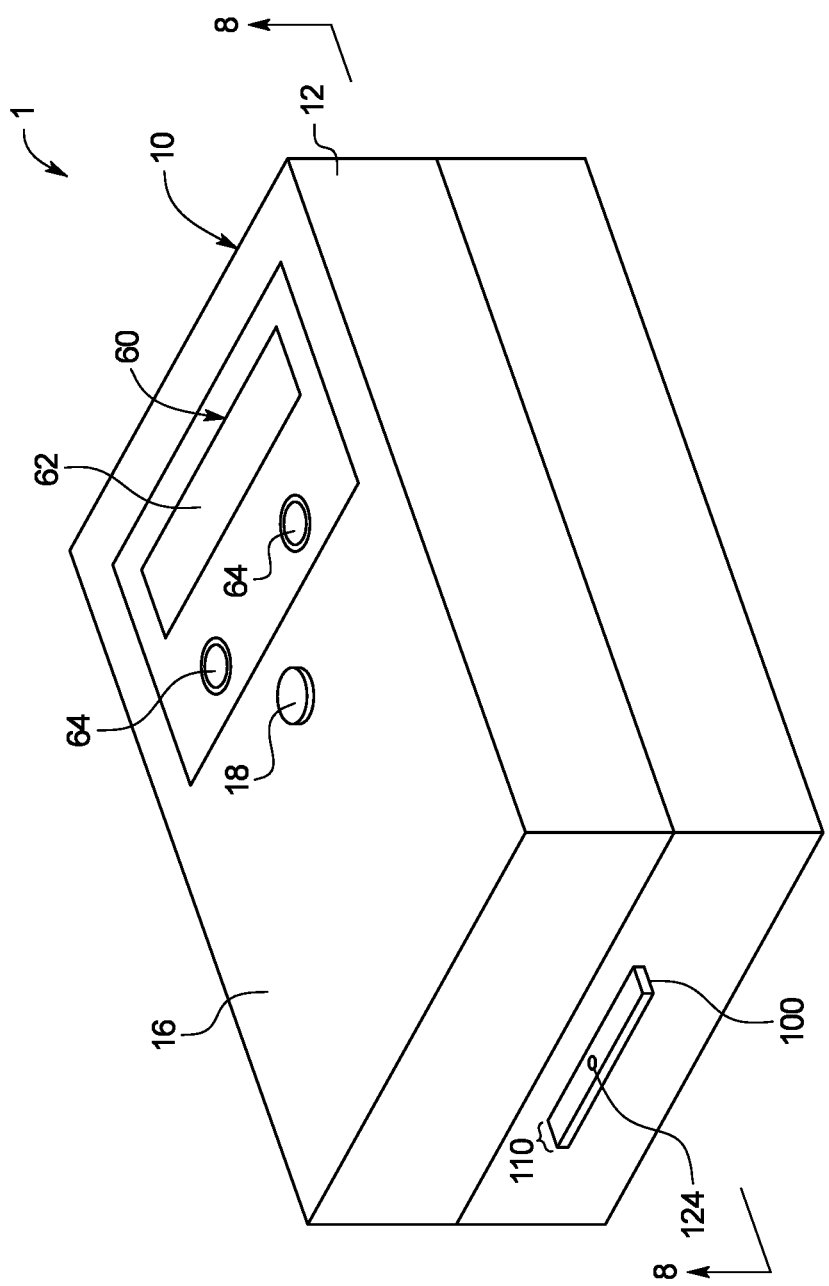
FIG. 7 is a top perspective view of the assay device of FIG. 1 with the test card of FIG. 3 inserted therein.
Figure 8:
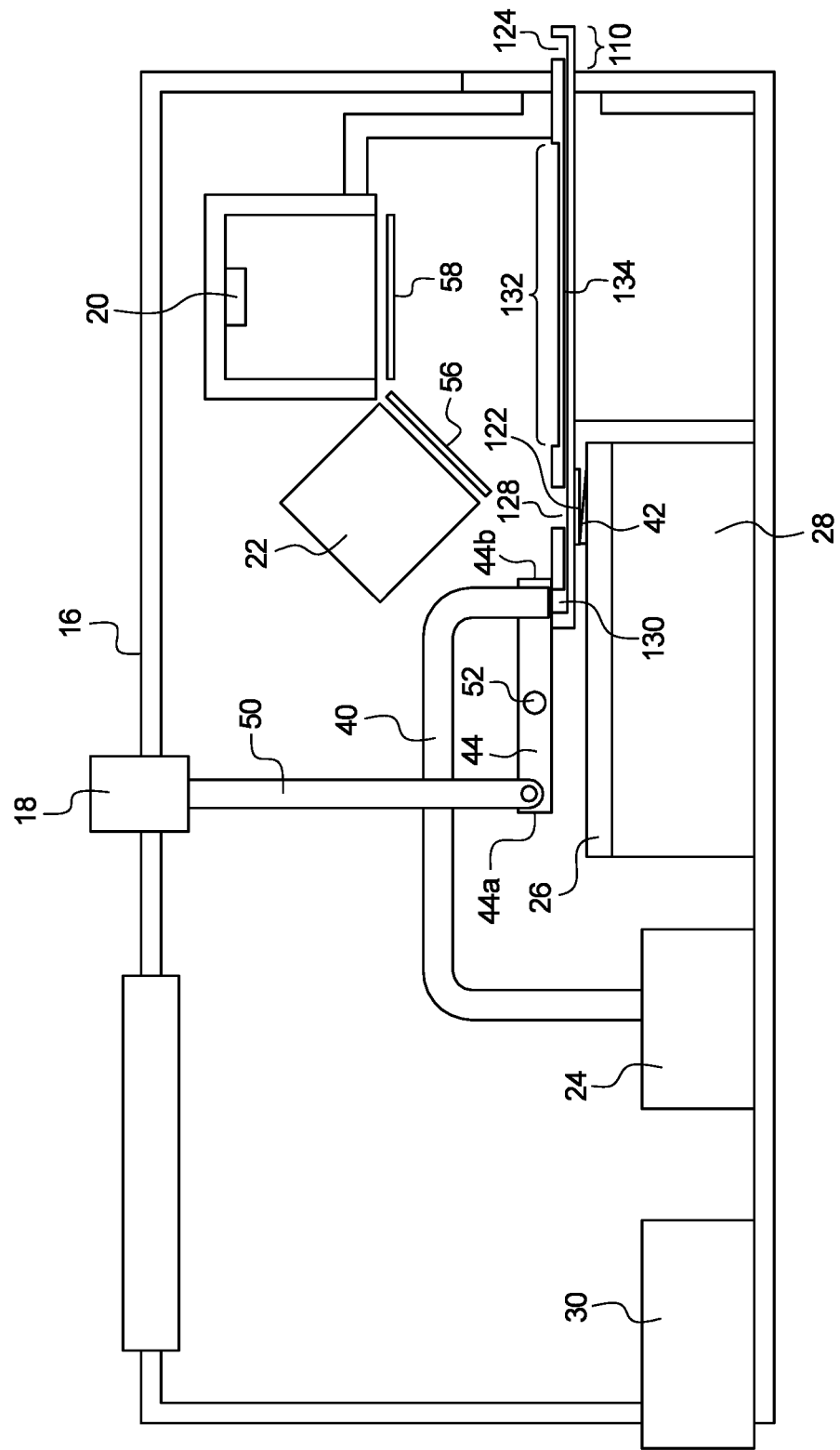
FIG. 8 is a cross-sectional view of the assay device and test card shown in FIG. 7.

FIG. 7 illustrates a perspective view of device 10 after test card 100 has been placed in slot 14, and FIG. 8 illustrates a cross-sectional view thereof. In the illustrated embodiment, test card 100 is inserted so that an inlet portion 110 of test card 100 including inlet port 124 is located outside of housing 12 when test card 100 is fully inserted into slot 14. In this embodiment, a user can place test card 100 into housing 12 and then inject a fluid sample into inlet port 124. In an alternative embodiment, test card 100 can be inserted into slot 14 after a fluid sample has been injected into inlet port 124. In another alternative embodiment, test card 100 can be inserted into slot 14 so that no portion of test card 100 lies outside of housing 12.

As illustrated, placement of test card 100 into slot 14 aligns several of the elements of device 10 with several of the elements of test card 100. For example, placement of test card 100 into slot 14 aligns camera imaging device 20 and light source 22 of device 10 with analysis port 132 on an upper surface 104 of test card 100 (and with reaction zone 166 within analysis port 132), pneumatic tube 40 of fluid actuation source 24 with outlet port 130 on the upper surface 104 of test card 100, and electrical contacts 42 of electrical contact device 26 with electrical contacts 122 of a printed circuit layer on the bottom surface 102 of test card 100.

In the illustrated embodiment, fluid actuation source 24 includes a pneumatic tube 40 that is sealed against outlet port 130 of test card 100 by block 44 when test card 100 is inserted into slot 14. Vacuum source 24 is configured to apply a negative pneumatic pressure or vacuum to outlet port 130 via pneumatic tube 40, which causes the fluid sample inserted into inlet port 124 to be pulled from mixing chamber 126 through fluid microchannel 134 towards outlet port 130.

For vacuum source 24 to operate effectively, pneumatic tube 40 must be completely sealed against outlet port 130. In an embodiment, pneumatic tube 40 can be sealed against outlet port 130, for example, via a rubber gasket at the end of pneumatic tube 40. In another embodiment, pneumatic tube 40 can be sealed against block 44, and block 44 can be sealed against outlet port 130, for example, via a rubber gasket at the end of an aperture in block 44.

In the illustrated embodiment, button 18 protruding from the top surface 16 of housing 12 assists in sealing pneumatic tube 40 against outlet port 130 to align fluid actuation source 24 with outlet port 130. As illustrated, button 18 is attached to a first side 44a of block 44 via rod 50, and pneumatic tube 40 is attached to a second side 44b of block 44. Block 44 is configured to pivot about pivot point 52. By pushing button 18 downward at first side 44a, second side 44b with pneumatic tube 40 is rotated upward, which allows outlet port 130 of test card 100 to slide underneath second side 44b. When button 18 is released, second side 44b rotates downward so that pneumatic tube 40 is sealed against outlet port 130. In an embodiment, button 18 is biased upward, for example by a spring force, so that block 44 is biased to the configuration shown in FIG. 8.

Once pneumatic tube 40 is sealed against outlet port 130, a negative pneumatic force can be applied to outlet port 130 from fluid actuation source 24. When the negative pneumatic force is applied, the fluid sample previously injected into inlet port 124 is pulled through fluid microchannel 134 towards outlet port 130. The fluid sample however is not pulled into pneumatic tube 40 due to the presence of capture port 128 between inlet port 124 and outlet port 130. Capture port 128 allows fluid to build up before it can reach outlet port 130 and/or pneumatic tube 40, which keeps device 10 sterile and protects the integrity of diagnostic system 1.

Figure 9:
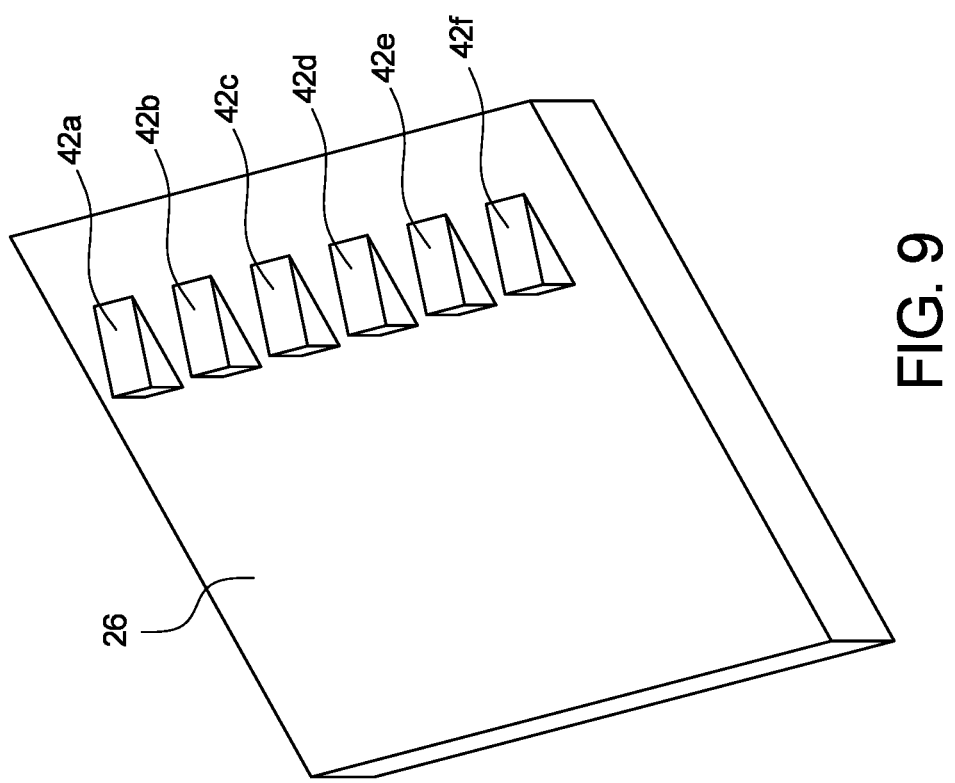
FIG. 9 is a top perspective view of an example embodiment of an electrical contact device according to the present disclosure.

As illustrated in FIG. 8, test card 100 is dimensioned so that electrical contacts 122 of test card 100 are placed in electrical contact with electrical contacts 42 of electrical contact device 26 when test card 100 is fully inserted into slot 14 so that pneumatic tube 40 is sealed against outlet port 130. FIG. 9 illustrates electrical contact device 26 in more detail. As illustrated, electrical contact device 26 includes a plurality of electrical contacts 42a, 42b, 42c, 42d, 42e, 42f that are configured to align with the plurality of electrical contacts 122a, 122b, 122c, 122d, 122e, 122f of test card 100, so that each of electrical contacts 42 of electrical contact device 26 of device 10 is aligned with a separate electrical contact 122 of test card 100. In the illustrated embodiment, electrical contact 42a makes electrical contact with electrical contact 122a, electrical contact 42b makes electrical contact with electrical contact 122b, electrical contact 42c makes electrical contact with electrical contact 122c, electrical contact 42d makes electrical contact with electrical contact 122d, electrical contact 42e makes electrical contact with electrical contact 122e, and electrical contact 42f makes electrical contact with electrical contact 122f. By applying a current to each of electrical contacts 42a, 42b, 42c, 42d, 42e, 42f individually, the electrodes on test card 100 can be controlled independently of each other, and measurements can be taken from each electrode. Those of ordinary skill in the art will recognize that more or less electrical contacts can be used on assay device 10 and/or test card 100 depending on the number of electrodes on test card 100 that assay device 10 is required to control.

In the illustrated embodiments, electrical contacts 42 protrude upwardly at an angle from electrical contact device 26 and are configured to retract towards electrical contact device 26 as they make contact with test card 100. FIGS. 2 and 9 illustrate electrical contacts 42 before insertion of test card 100, where electrical contacts 42 are fully extended from electrical contact device 26. FIG. 8 illustrates electrical contacts 42 after insertion of test card 100, where the electrical contacts 42 have been pushed towards or into electrical contact device 26 by test card 100. By forming electrical contacts 42 as illustrated, it can be ensured that electrical contact is made between electrical contacts 42 of electrical contact device 26 and electrical contacts 122 of test card 100. Although the illustrated electrical contacts 42 are shown to have a triangular shape, those of ordinary skill in the art will recognize that other shapes and configurations are possible.

With the electrical contacts 42 and 122 aligned, device 10 can perform several functions. Before beginning an analysis, controller 28 can ensure that the fluid sample has been properly pulled through microchannel 134 and into target zone 166. By applying a current to electrical contact 42a aligned with electrical contact 122a and/or electrical contact 42f aligned with electrical contact 122f, controller 28 can activate the capacitor of first fluid detection zone 150 and measure the corresponding capacitance to ensure that the fluid sample has flowed through first fluid detection zone 150. Likewise, by applying a current to electrical contact 42c aligned with electrical contact 122c and/or electrical contact 42d aligned with electrical contact 142d, controller 28 can activate the capacitor of second fluid detection zone 154 and measure the corresponding capacitance to ensure that the fluid sample has flowed through second fluid detection zone 154. If fluid is located within both first fluid detection zone 150 and second fluid detection zone 154, controller 28 can determine that fluid from the fluid sample is located within target zone 166.

Once it is determined that fluid is located within target zone 166 of microchannel 134, controller 28 can apply a current to electrical contact 42b aligned with electrical contact 122b and to electrical contact 42e aligned with electrical contact 122e to heat the fluid sample within target zone 166 and cause a PCR to begin. During the PCR, current is applied to the electrodes 162a and 162b located adjacent to target zone 166 to raise the temperature of the fluid sample located within target zone 166. The desired temperature for different PCR's can vary. The temperature within target zone 166 can be monitored by a temperature sensor located within assay device 10 or test card 100 at a location adjacent to target zone 166, and controller 28 can receive feedback from the temperature sensor and adjust the current applied to electrical contact 42b and/or electrical contact 42e based on the feedback to maintain a desired temperature for the PCR.

Camera imaging device 20 is configured to record a series of still images of the fluid sample within target zone 166 during the PCR and/or a video of the fluid sample within target zone 166 during the PCR. In an embodiment, camera imaging system 20 includes a high sensitivity and dynamic range complementary metal-oxide semiconductor (CMOS) camera sensor which allows for general imaging of a PCR within target zone 166 of fluid microchannel 134 of test card 100. Camera imaging device 20 allows the PCR to be monitored in real time, by taking still and/or video images of the PCR within target zone 166 of fluid microchannel 134 over a period of time.

In the illustrated embodiment, light source 22 is configured to project a fluorescent excitation light on target zone 166 of fluid microchannel 134 while the PCR takes place, and while camera imaging device 20 takes still and/or video images of the PCR. When the PCR is illuminated with a fluorescent excitation light, controller 28 can make fluorescence measurements based on the images taken by camera imaging device 20, which can be analyzed by controller 28 to determine whether the fluid sample tests positive or negative for a particular bacteria or virus. Camera imaging device 20 also enables a variety of optical measurements to be taken in addition to fluorescence measurements, for example, turbidity and object detection measurements.

As illustrated, device 10 can include an excitation optical filter 56 located beneath light source 22, and an emission optical filter 58 located beneath camera imaging system 20. In an embodiment, excitation optical filter 56 functions to ensure only light of a wavelength below a cut off frequency of 500 nanometers is allowed to be incident to the test card 100 (short pass filter), and emission optical filter 58 functions to ensure only light greater than a cut off frequency 500 nanometers is allowed to be incident to camera imaging device 20 (long pass filter). These values can change depending on the emission spectra of a specific fluorescent reaction. In addition, by utilizing a long pass emission filter, a fluorescent reaction which has two emission peaks greater than the cut off frequency of the emission filter can be detected using a color camera sensor using a Bayer color filter.

An example embodiment of how controller 28 can analyze a fluid sample is described in more detail in U.S. application Ser. No. 15/185,714, entitled "Camera Imaging System for a Fluid Sample and Method of Using Same", the entire disclosure of which, and specifically the analysis disclosure, is incorporated herein by reference and relied upon. Those of ordinary skill in the art will recognize other analyses that can be performed using camera imaging device 20.

Device 10 is configured to accept a plurality of different types of test cards 100 intended for different types of assays. For example, a first type of test card can relate to a PCR, while a second type of test card can relate to flow cytometry. Assay device 10 is configured to accept different test cards 100, recognize the type of test card 100 at the time of insertion into slot 14, and run the appropriate assay for the test card without specific instructions by the user.

In an embodiment, each test card 100 includes a code, for example, a QR code or barcode, to identify the type of assay that the test card 100 is intended for. Assay device 10 can include a corresponding code reader that is positioned to align with the code on test card 100 when test card 10 is inserted into slot 14. In another embodiment, device 10 can include a user interface 60 including a display 62 and buttons 64. A user can enter a code written on test card 100 into user interface 60, and device 10 can recognize the code and run the appropriate test.

Each of the different types of test cards includes electrical contacts 122 in the same locations, although the electrical contacts can lead to different electrodes configured for different purposes. For example, in the embodiment illustrated in FIGS. 5 and 6, test card 100 has six electrical contacts corresponding to a target zone 166 and two fluid detection zones 150, 154. In another embodiment, for example, test card 100a can include six electrical contacts corresponding to three different target zones 166, or can include more or less than six electrical contacts corresponding to a target zone and different types of sensors such as capacitance and temperature sensors. By reading the code on each test card 100, controller 28 can determine the current to apply to each of electrical contacts 122 via electrical contacts 42 to run the assay desired by the user based on the card inserted.

For example, if test card 100 of FIGS. 3 to 5 is inserted into slot 14, controller 28 can read the code on test card 100 and determine that a single PCR is intended to be run within a single target zone 166. Controller 28 will therefore apply the desired current to electrical contacts 122c and 122d via electrical contacts 42c and 42d to cause the PCR to occur within target zone 166.

If an alternative embodiment of a test card 100a is instead inserted into slot 14, controller 28 can read the code on test card 100a and determine, for example, that a flow cytometry assay or an ELISA is intended to be run. Flow cytometry and ELISA tests do not require the fluid in target zone 166 to be heated to multiply molecules by diffusion, so the electrodes can be used for other purposes or omitted completely.

Figure 10:
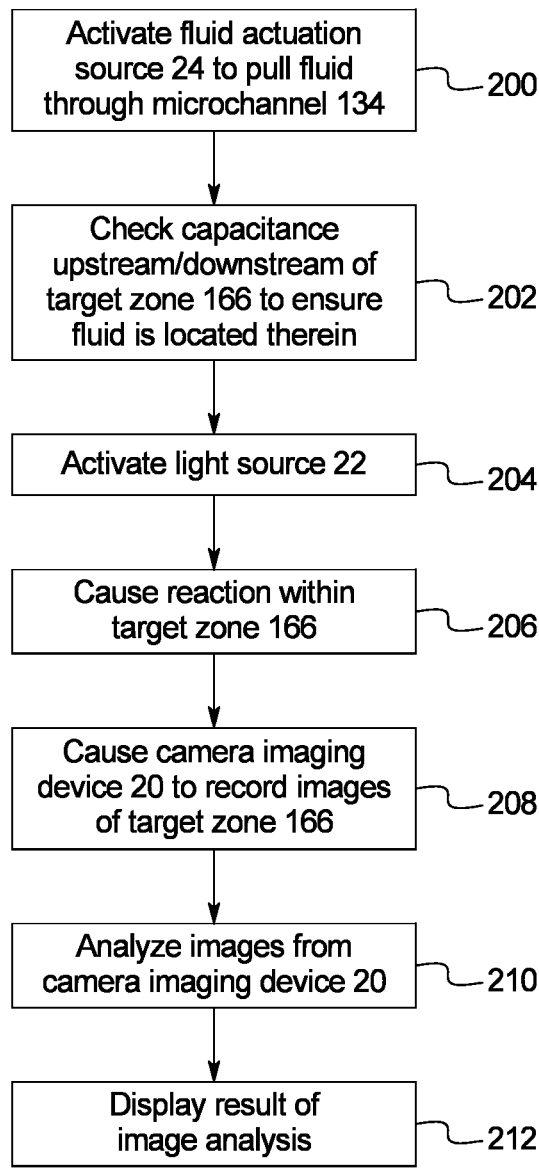
FIG. 10 illustrates an example embodiment of a control method that can be used to analyze a fluid sample according to the present disclosure.
Figure 11:
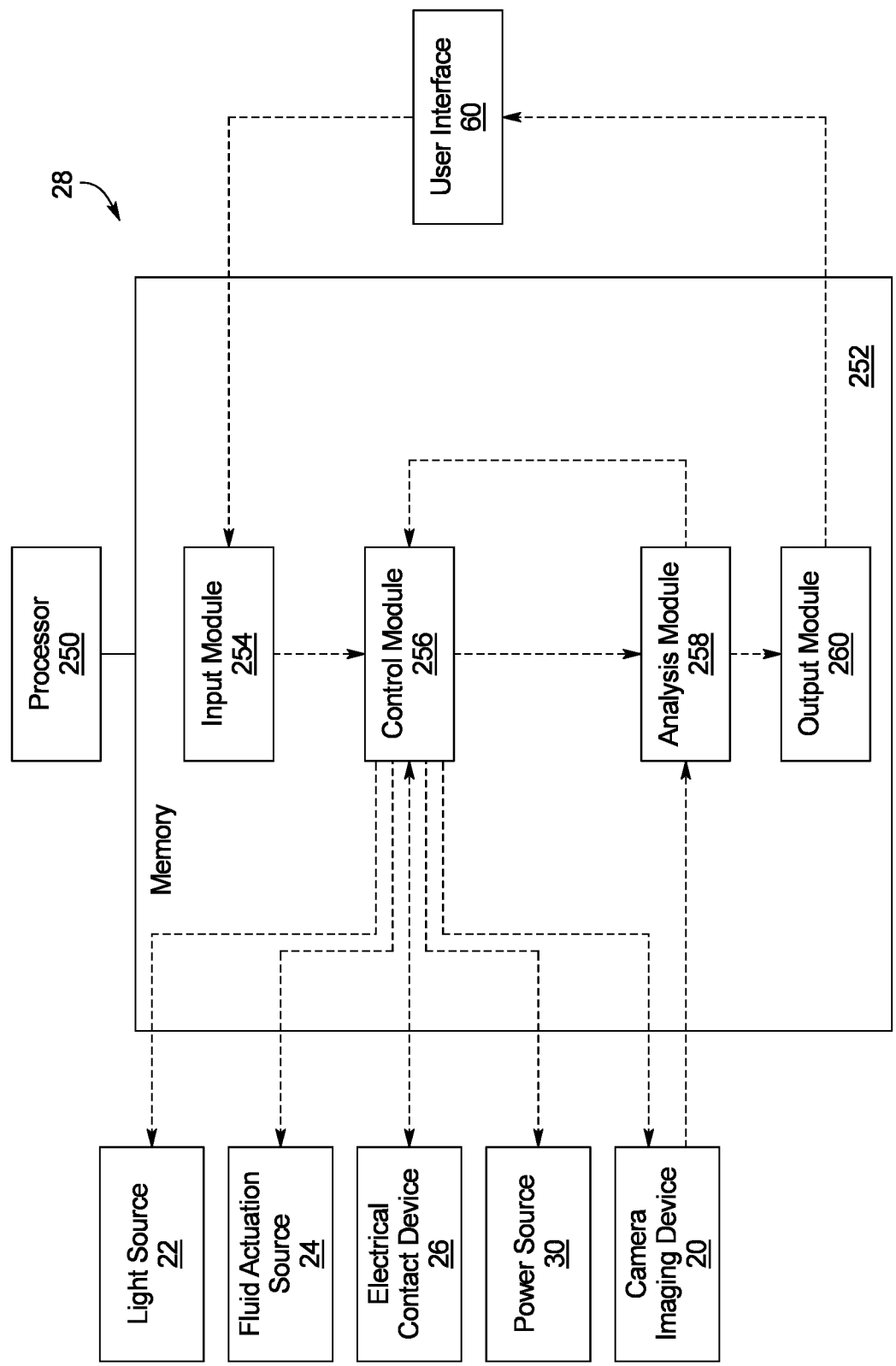
FIG. 11 illustrates an example embodiment of a controller that can perform the method of FIG. 10.

FIG. 10 illustrates an example embodiment of a control method that can be used by controller 28 to perform and analyze a reaction as described herein, and FIG. 11 illustrates an example embodiment of a controller 28 that can perform the method of FIG. 10. As illustrated, controller 28 can include a processor 250 and a memory 252, which can include a non-transitory computer readable medium. Memory 252 can include, for example, an input module 254, a control module 256, an analysis module 258, and an output module 260. Processor 250 can run the modules 252, 254, 256, 258 in accordance with instructions stored on memory 252. The broken lines in FIG. 8 illustrate the electrical connections between the modules 252, 254, 256, 258 of controller 28 and various elements of device 10. It should be understood by those of ordinary skill in the art that the illustrated modules and/or additional modules can be connected to the elements shown and/or additional elements.

The process begins by loading a test card 100 and/or a fluid sample into device 10. The fluid sample can be mixed with a reagent before injection into test card 100 and/or device 10, or can be mixed with a reagent within mixing chamber 26 of test card 100. In an embodiment, the reagent includes a PCR inhibitor-resistant polymerase along with a specific mixture of reverse transcriptase (in the case of RNA targets) and surfactants/dispersants to allow for rapid sample dispersion and lysing. In an embodiment, the reagent mix can include, for example, oligonucleotide primers, dNTP's DNA polymerase and other chemicals to assist the PCR. It is important to have a correct ratio of fluid sample to final PCR volume, because if the correct ratio is not maintained, the PCR will take too long or fail. In an embodiment, a PCR inhibitor resistant polymerase can be generated from mutant TAq.

Using user interface 60, a user can begin the reaction. As explained above, device 10 can indicate what type of test is to be run by reading a code on the test card. Alternatively, a user can choose an analysis to run on the fluid sample using the display 62 and buttons 64 of user interface 60. In an embodiment, a user can cycle through a plurality of tests on display 62 using buttons 64 and choose one or more test to run. The plurality of tests can include, for example, a PCR analysis, a cytometry analysis and/or an enzyme-linked immunosorbent assay (ELISA) analysis.

Input module 254 is configured to receive the user inputs inputted into user interface 60 and communicate the user inputs to control module 256. Input module 254 can also receive additional information via user interface 60 and/or by the preprogramming of controller 28, for example, (i) real-time PCR crossover threshold value information; (ii) maximum fluorescence information; and (iii) melting curve inflection temperature information.

Once a test card 100 and/or fluid sample has been loaded into device 10, control module 256 of controller 28 begins the control method at step 200 by causing fluid actuation source 26 to pull fluid through microchannel 134. In the illustrated embodiment, fluid actuation source 26 applies a negative pneumatic force to outlet port 130 via pneumatic tube 40 to pull fluid through microchannel 134. In an alternative embodiment, fluid actuation source can include one or more other type of pump in fluid communication with microchannel 134.

After fluid actuation source 26 has been activated, but before any reaction within target zone 166 begins, control module 256 at step 202 can verify that fluid is located within target zone 166 by monitoring the capacitance of microchannel 134 at one or more locations upstream and/or downstream of target zone 166 via electrodes 160 and 164. If fluid is detected in microchannel 134 upstream and downstream of target zone 166 by electrodes 160 and 164, control module 256 can verify that fluid is located within target zone 166, activate light source 22 at step 204, and begin a reaction at step 206.

If a PCR is being run, control module 256 begins the reaction at step 206 by causing power source 30 to send a current to electrodes 162a and 162b located adjacent to target zone 166 via electrical contact device 26 to cause the fluid within target zone 166 to be heated. As the fluid sample is heated, the nucleic acid molecules in the fluid sample multiply by diffusion, as explained in more detail in U.S. application Ser. No. 15/185,714, entitled "Camera Imaging System for a Fluid Sample and Method of Using Same".

At the same time that the fluid sample is being heated within target zone 166 so that the nucleic acid molecules multiply by diffusion, control module 256 at step 208 can cause camera imaging device 20 to record a plurality of images of the reaction within target zone 166 through analysis port 132. The plurality of images can then be sent to analysis module 208 for analysis at step 210. In an embodiment, test card 100 includes a transparent material that allows images to be taken of target zone 166 of fluid microchannel 134 even though a layer of polymer material is located between camera imaging device 20 and fluid microchannel 134.

At step 210, analysis module 258 analyzes the images taken by camera imaging device 20 to determine whether the fluid sample tests positive or negative for a bacteria or virus. The type of analysis performed by analysis module at step 210 will depend on the type of assay being run on the fluid sample.

If the assay being run on the fluid sample is a PCR, then analysis module 258 can analyze the images, for example, by measuring fluorescence as nucleic molecules multiply by diffusion.

If the assay being run on the fluid sample is a flow cytometry analysis, then analysis module 258 can also analyze the images by measuring fluorescence. The cytometry analysis can differ from the PCR analysis, for example, because the fluid in target zone 166 does not need to be heated to multiply molecules by diffusion, so step 206 can be skipped. With a cytometry analysis, analysis module 258 can analyze the fluid sample within target zone 166, for example, by analyzing cell size, cell count, cell morphology (shape and structure), cell cycle phase, DNA content, and the existence or absence of specific proteins on cell surfaces. In an embodiment, analysis module 258 can also measure droplets in the case of droplet based reactions.

If the assay being run on the fluid sample is an ELISA analysis, then again the fluid in target zone 166 does not need to be heated to multiply molecules by diffusion, so step 206 can be skipped. With an ELISA analysis, analysis module 258 can analyze the fluid sample within target zone 166, for example, by measuring the concentration of an analyte in the fluid sample using a colorimetric analysis. In an embodiment, a colorimetric analysis can include measuring the color intensities between target zones to determine the transmittance of light from each reaction chamber on the test card and determine the relative concentration of a specific analyte in each reaction chamber.

At step 212, analysis module 258 determines based on the analysis whether the fluid sample has tested positive or negative for a bacteria or virus. In an embodiment, display 62 can be configured to display a result of the analysis of analysis module 258 of controller 28. It is contemplated for the result to be a simple "positive" or "negative" result for the assay, so that device 10 can be quickly and easily used without the need for specialized training. User interface 60 is designed so that a user with minimal training can understand how to use both the device 10 and test cards 100. In an embodiment, analysis module can also display viral or bacterial load and the raw test data. In the case of a PCR reaction this includes amplification curves, melting curves, melting temperatures, fluorescence crossover cycle, etc.

Power source 30 is configured to provide power to all of the electrical components of device 10, for example, user interface 60, camera imaging device 20, light source 22, fluid actuation source 24, electrical contact device 26 and controller 28. In an embodiment, power source 30 includes a rechargeable or replaceable battery. In another embodiment, power source 30 can be plugged into a wall outlet to provide power or to be recharged by the wall outlet. Preferably, power source 30 is configured to store power so that device 10 can be used when there is no external power source present.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed. No language in the specification should be construed as indicating any non-claimed element essential to the practice of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of the disclosure are described herein, including the best mode known to the inventors for carrying out the disclosure. Of course, variations on those preferred embodiments will become apparent to those of ordinary skill in the art upon reading the foregoing description. The inventor expects those of ordinary skill in the art to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

Further, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention is claimed as follows:

1. An analyzer apparatus for analyzing a fluid sample, the apparatus comprising:
    a slot configured to receive a test card;
    a fluid actuation source configured to engage a port on the test card after the test card is received within the slot, the fluid actuation source configured to apply pressure to the port to cause the fluid sample to move along a microchannel of the test card to enable one or more assays to be performed;
    an electrical contact device including a plurality of electrical contacts, the plurality of electrical contacts configured to contact a plurality of test card electrical contacts, the plurality of electrical contacts configured for performing the one or more assays on the test card;
    a memory storing a plurality of assays that are available to be performed by the analyzer apparatus, the assays comprising at least the following assays: (a) a nucleic acid amplification assay, (b) an immunoassay, (c) an ion selective assay, and (d) an image cytometry assay; and
    a controller electrically connected to the electrical contact device and the fluid actuation source, the controller configured to:
        detect insertion of the test card into the slot,
        receive an indication as to which one or more assays are to be performed,
        cause the fluid actuation source to move the fluid sample into one or more regions on the test card to enable the one or more assays to be performed,
        cause the plurality of electrical contacts to provide power to the test card for performing the one or more assays, and
        determine at least one test result based on the performed assays.

2. The apparatus of claim 1, further comprising a pneumatic tube that fluidly connects the fluid actuation source to the output port of the test card.

3. The apparatus of claim 1, wherein the fluid actuation source includes at least one of a pump or a vacuum source.

4. The apparatus of claim 1, further comprising a memory storing a plurality of assays that are available to be performed by the analyzer apparatus, the assays corresponding to at least one of (a) a capacitance-based assay, (b) a fluorescence-based assay, or (c) a colorimetric-based assay.

5. The apparatus of claim 1, wherein the controller is further configured to cause a user interface or a display device to display the at least one test result.

6. The apparatus of claim 1, wherein the at least one test result is indicative as to whether the fluid sample has:
   tested positive or negative for a bacteria or a virus, or
   tested positive or negative for a presence or a threshold amount of an analyte or chemical species.

7. The apparatus of claim 1, further comprising:
   a sensor for measuring a temperature of the fluid sample at a target zone of the test card;
   a light source emitting one or more specific wavelengths of light and configured to illuminate at least the target zone of the test card; and
   a camera configured to record an image of at least the target zone of the test card,
   wherein the controller is configured to use the sensor, the light source, and the camera based on which of the one or more assays are to be performed.

8. An analyzer apparatus for analyzing a fluid sample, the apparatus comprising:
   a sensor for measuring a temperature of the fluid sample at a target zone of a test card;
   a light source emitting one or more specific wavelengths of light and configured to illuminate at least the target zone of the test card;
   a camera configured to record one or more images of at least the target zone of the test card;
   a plurality of pairs of electrical contacts to enable an assay to be performed on the test card, the plurality of pairs of electrical contacts configured to provide current to the test card; and
   a controller electrically connected to the code reader, the sensor, the light source, the camera and the plurality of pairs of electrical contacts,
   wherein the analyzer apparatus is configured to include at least the following diagnostic modalities on the fluid sample located on the test card:
      (i) heat the fluid sample using the controller in conjunction with a first pair of electrical contacts,
      (ii) perform a fluorescence measurement using the controller in conjunction with the light source and the camera,
      (iii) perform a capacitance or a voltage measurement using the controller in conjunction with a second pair of electrical contacts, and
      (iv) perform a temperature measurement using the controller in conjunction with the sensor,
   wherein the analyzer apparatus is configured to provide at least the following assays:
      (a) a nucleic acid amplification assay using (i), (ii), and (iv),
      (b) an immunoassay using (ii) and a colormetric analysis,
      (c) an ion selective assay using (iii), and
      (d) an image cytometry assay using (ii),
   wherein the controller is configured to perform on the fluid sample (a) to (d) individually or at least two of (a) to (d) simultaneously in parallel and/or in series based on a selected assay to obtain at least one test result.

9. The apparatus of claim 8, wherein the nucleic acid amplification assay includes a polymerase chain reaction ("PCR") assay, the immunoassay includes an enzyme-linked immunosorbent assay ("ELISA"), and the ion selective assay includes an agglutination-PCR assay.

10. The apparatus of claim 8, wherein the image cytometry assay is configured to analyze at least one of a cell size, a cell count, a cell morphology (shape and/or structure), a cell cycle phase, DNA content, or an existence or absence of specific proteins on cell surfaces.

11. The apparatus of claim 8, wherein the analyzer apparatus is configured to perform a fluorescence measurement using the controller in conjunction with the light source and the camera, wherein the analyzer apparatus is configured to provide an image cytometry assay, wherein the image cytometry assay includes a droplet based reaction of the fluid sample.

12. The apparatus of claim 8, wherein the controller is further configured to cause a user interface or a display device to display the at least one test result.

13. The apparatus of claim 8, further comprising a user interface for receiving a user selection of an assay or a code from the test card that is indicative of the assay to perform.

14. The apparatus of claim 8, further comprising a code reader configured to read a code on the test card, wherein the controller is configured to:
   receive a signal from the code reader that is indicative of the code on the test card,
   cause at least one of (a) to (d) to be performed based on the code.

15. The apparatus of claim 8, wherein the one or more specific wavelengths of light emitted by the light source includes fluorescence excitation light.

16. The apparatus of claim 8, wherein the at least one test result is indicative as to whether the fluid sample has tested positive or negative for a bacteria or a virus.

17. The apparatus of claim 8, wherein the at least one test result is indicative as to whether the fluid sample has tested positive or negative for a presence or a threshold amount of an analyte or chemical species.

18. The apparatus of claim 8, further comprising a vacuum source for fluidly coupling with a microchannel on the test card, the vacuum source configured to pull the fluid sample at least into the target zone after insertion of the test card into a slot of the analyzer apparatus.

19. The apparatus of claim 8, further comprising a pump for fluidly coupling with a microchannel on the test card, the pump configured to move the fluid sample at least into the target zone after insertion of the test card into a slot of the analyzer apparatus.

* * * * *